(12) United States Patent
Pohl et al.

(10) Patent No.: US 7,547,801 B2
(45) Date of Patent: Jun. 16, 2009

(54) PROCESS FOR THE CONTINUOUS PREPARATION OF ISOCYANATES

(75) Inventors: Fritz Pohl, Brunsbuttel (DE); Ricardo Serra, Krefeld (DE); Matthias Ehlers, Mame (DE); Jeffrey S. Bolton, Dusseldorf (DE); Gary B. Solak, League City, TX (US); Kirk J. Bourgeois, Baytown, TX (US); Gregory L. McCullough, Highlands, TX (US); Amber R. Hicks, Manvel, TX (US); Richard G. Hillman, Houston, TX (US); James E. Sager, Highlands, TX (US); Xiaoyan Wang, League City, TX (US); Spotswood Miller, Friendswood, TX (US); Ralf Ochel, Seabrook, TX (US); Sara DeLucia, Pittsburgh, PA (US)

(73) Assignees: Bayer MaterialScience LLC, Pittsburgh, PA (US); Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 11/474,795

(22) Filed: Jun. 26, 2006

(65) Prior Publication Data

US 2007/0299279 A1 Dec. 27, 2007

(51) Int. Cl.
  *C07C 249/00* (2006.01)
(52) U.S. Cl. .................................................... 560/347
(58) Field of Classification Search ........................ None
  See application file for complete search history.

(56) References Cited

U.S. PATENT DOCUMENTS

| | | | |
|---|---|---|---|
| 3,226,410 A | 12/1965 | Hettich et al. ................ 260/453 |
| 3,287,387 A | 11/1966 | Denton et al. ................ 260/453 |
| 3,321,283 A | 5/1967 | Ewald ........................ 23/283 |
| 3,544,611 A | 12/1970 | Michelet et al. ............. 260/453 |
| 3,947,484 A | 3/1976 | Mitrowsky et al. ..... 260/453 PH |
| 3,978,105 A | 8/1976 | Fuchs et al. ........... 260/453 PH |
| 4,096,165 A | 6/1978 | Meyers ................. 260/453 PH |
| 4,128,569 A | 12/1978 | Horn et al. ............ 260/453 PH |
| 4,289,732 A | 9/1981 | Bauer et al. ................. 422/224 |
| 4,419,295 A | 12/1983 | Hennig et al. ......... 260/453 PH |
| 4,549,991 A | 10/1985 | Disteldorf et al. ..... 260/453 PH |
| 4,581,174 A | 4/1986 | Ohlinger et al. ............. 560/347 |
| 4,847,408 A | 7/1989 | Frosch et al. ................ 560/347 |
| 4,851,570 A | 7/1989 | Zaby et al. ................... 560/347 |
| 4,851,571 A | 7/1989 | Sauer et al. ................. 560/347 |
| 5,117,048 A | 5/1992 | Zaby et al. ................... 560/347 |
| 5,449,818 A | 9/1995 | Biskup et al. ............... 560/347 |
| 5,516,935 A | 5/1996 | Bischof et al. .............. 560/347 |
| 5,599,968 A | 2/1997 | Bankwitz et al. ............ 560/347 |
| 5,633,396 A | 5/1997 | Bischof et al. .............. 560/347 |
| 5,925,783 A | 7/1999 | Jost et al. .................... 560/347 |
| 5,931,579 A | 8/1999 | Gallus et al. .............. 366/163.2 |
| 6,225,497 B1 | 5/2001 | Becker et al. ............... 560/347 |
| 6,576,788 B1 | 6/2003 | Penzel et al. ................ 560/333 |
| 2006/0025556 A1 * | 2/2006 | Koch et al. .................... 528/44 |

FOREIGN PATENT DOCUMENTS

| | | |
|---|---|---|
| CA | 1317306 | 5/1993 |
| DE | 844 896 | 9/1952 |
| DE | 1 175 666 | 8/1964 |
| DE | 1 192 641 | 5/1965 |
| DE | 1 768 439 | 11/1971 |
| DE | 2 058 032 | 5/1972 |
| DE | 132 340 | 9/1978 |
| DE | 300 168 | 5/1992 |
| DE | 100 27 779 A1 | 12/2001 |
| FR | 69 428 | 11/1958 |
| GB | 763535 | 12/1956 |
| GB | 827376 | 2/1960 |
| GB | 901377 | 7/1962 |
| GB | 1034285 | 6/1966 |
| GB | 1 212 249 | 11/1970 |
| GB | 1 238 669 | 7/1971 |
| GB | 1 255 637 | 12/1971 |
| GB | 1 341 311 | 12/1973 |
| GB | 1077031 | 7/1975 |
| JP | 57-48954 | 3/1982 |
| WO | 2004/056756 A1 | 7/2004 |

\* cited by examiner

*Primary Examiner*—Karl J Puttlitz
(74) *Attorney, Agent, or Firm*—Lyndanne M. Whalen

(57) ABSTRACT

Isocyanates are produced by reacting an organic amine with phosgene in process which includes at least three stages. The first stage is carried out in a dynamic mixer. The second stage is carried out in at least one reactor. The third stage is carried out in at least one material separating apparatus. The pressure in the reactor of the second stage must be greater than or equal to the pressure in the dynamic mixer. The pressure in the third stage material separating apparatus must be lower than the pressure in the second stage reactor.

10 Claims, No Drawings

PROCESS FOR THE CONTINUOUS PREPARATION OF ISOCYANATES

BACKGROUND OF THE INVENTION

The present invention relates to a process for the preparation of isocyanates by the reaction of organic amines with phosgene in which the reaction is conducted in at least three stages. The first stage is carried out in a dynamic mixer. The second stage is conducted in at least one reactor. The third stage is conducted in at least one material separating apparatus. The pressure in the reactor of the second stage is greater than or equal to the pressure in the dynamic mixer, and the pressure in at least one material separating apparatus being less than the pressure in the reactor of the second stage.

It is known to prepare isocyanates from amines and phosgene. Depending on the type of amines, the reaction is carried out either in the gas phase or in the liquid phase and either batchwise or continuously (W. Siefken, Liebigs Ann. 562, 75 (1949)).

The continuous preparation of organic isocyanates by the reaction of primary organic amines has been described many times and is carried out on the industrial scale. See, for example, Kunststoffhandbuch, volume 7 (Polyurethane), 3rd revised edition; and Carl Hanser Verlag, Munich-Vienna, p. 76 et seq. (1993). In particular, the aromatic isocyanates TDI (toluene diisocyanate); MDI (methylenediphenyl diisocyanate), PMDI (polymethylenepolyphenylene polyisocyanate) and mixtures of the last two; and the aliphatic isocyanates HDI (hexamethylene diisocyanate) and isophorone diisocyanate (IPDI), are prepared worldwide on an industrial scale.

Modern industrial syntheses of the aromatic diisocyanates MDI and TDI and the aliphatic diisocyanates HDI and IPDI are carried out almost exclusively by continuous processes. A continuous process for carrying out the reaction in several continuous-flow vessels can be found, e.g., in DE-A-844 896.

The continuous embodiment of the process normally takes place in two stages. In the first stage of the phosgenation, the amine is reacted with phosgene to give the corresponding carbamoyl chloride, hydrogen chloride and amine hydrochloride. The reaction between amine and phosgene is very rapid and strongly exothermic and proceeds even at very low temperatures. To minimize by-product and solid formation, the amine and phosgene, both optionally in organic solvent, must therefore be mixed rapidly, so the first phosgenation stage normally takes place in a mixer, which is frequently a nozzle. In the second stage of the phosgenation, the carbamoyl chloride decomposes to form the desired isocyanate and hydrogen chloride and the amine hydrochloride is phosgenated to form the carbamoyl chloride. The temperature of the second phosgenation stage is normally higher than that of the first.

The reaction of amine and phosgene in the liquid phase is very rapid at all the industrially conventional temperatures and pressures, so a good mixing of the reactants is sought in order to suppress secondary reactions. The phosgenation of primary amines in a stirred-tank reactor as the first stage of the phosgenation has accordingly been described many times.

Mixers can basically be divided into dynamic mixers (e.g. stirrers, turbines or rotor-stator systems) and static mixers (e.g., Kenics mixers, Schaschlik mixers or SMV mixers, as well as jet mixers such as nozzles or T mixers (Fortschr. Verf. Technik 23, 1985, 373; Ind. Eng. Chem. Res. 26, 1987, 1184)).

The mixers known to be useful in such processes include nozzles such as annular slot nozzles (DE-A-17 92 660), annular die nozzles (DE-A-37 44 001), smooth jet mixing nozzles (EP-A-0 065 727), fan jet nozzles (DE-A-29 50 216), angle jet chamber nozzles (DD-A-300 168), triple stream nozzles (DD-A-132 340), counter-current mixing chambers (DE-PS 1 146 872), Pitot nozzles (FR-A-69 428) and Venturi mixing nozzles (DE-AS 1 175 666). In-line mixers (U.S. Pat. No. 3,321,283), centrifugal or reaction mixing pumps (EP-A-0 291 819), tubular reactors (U.S. Pat. No. 3,226,410) or microstructure mixers (EP-A-0 928 785) are also known.

DD-A-132 340 describes a process for the phosgenation of amines under pressure and elevated temperature, in the presence of a homogeneous solvent, to give mono-, di- and polyisocyanates. In this process, an amine/monochlorobenzene mixture and a phosgene/monochlorobenzene mixture, split into several partial streams, are introduced in parallel into a reactor. A part of the phosgene/mono-chlorobenzene mixture is introduced centrally and the amine/monochlorobenzene mixture is introduced around this central stream. The amine/monochlorobenzene mixture in turn is enclosed by a phosgene/monochlorobenzene mixture. By way of example, the polyamine/monochlorobenzene mixture is fed annularly into the phosgenation reactor at 150° C. Before entering the reactor, the mixture is set into a rotating motion by means of an appropriate swirling device. A phosgene/monochlorobenzene mixture heated to 150° C. is introduced into the reactor as co-reactant, in and around the polyamine/monochlorobenzene mixture. The relative speed of the two co-reactants is approx. 15 m/s.

EP-A-0 830 894 describes a mixer reactor for the phosgenation of primary amines in which the inlet for one material is formed in the axis of the mixing chamber and the inlet for the (at least one) other material takes the form of a large number of nozzles arranged with rotational symmetry relative to the axis of the mixing chamber. Each of the nozzles has a bolt displaceable in the direction of the nozzle axis. The bolt is capable of freeing the nozzle of adhering solids.

Many apparatuses have also become established for the second phosgenation stage, which is optionally used simultaneously as a phase separation tank. The preparation of isocyanates from the corresponding amines by phosgenation takes place in stirred-tank reactors (e.g., DE-OS 14 68 445), series of stirred-tank reactors (DE-PS 844 896), packed reaction columns (e.g., WO-A-99/54289) or non-packed columns (e.g., Ullmanns Encyklopädie der technischen Chemie, 4th edition (1977), volume 13, page 351 et seq.). Loop reactors are also used to create a recirculation system so as to allow sufficient residence time for a complete conversion in the case of a limited reaction volume (or holdup).

The isocyanate synthesis commonly takes place in the first stage at a very low temperature and in the second stage at a markedly higher temperature in a holding apparatus. This procedure is frequently termed cold-hot phosgenation and is described, e.g., in W. Siefken, Liebigs Annalen der Chemie 562 (1949), page 96. Firstly, a suspension of the carbamoyl chloride and amine hydrochloride intermediates is prepared at a low temperature, especially 0° C. or room temperature, but not exceeding 60° C., and this suspension is then converted to the isocyanate at higher temperatures, especially in the range between 100 and 200° C., in a holding apparatus. Such two-stage processes are described in Kunststoffhandbuch, volume 7, Carl Hanser Verlag, Munich-Vienna, p. 76 et seq. (1993), and, e.g., in patents DE-A-20 58 032, DE-A-21 53 268 and DE-A-1 233 854.

A disadvantage of the two-stage procedure with a low temperature in the first stage and a high temperature in the second stage (cold-hot phosgenation) is the low reaction rates and hence low space-time yields due to the low temperatures in the first reaction stage. The low temperatures (high solubility of phosgene) and long reaction times (large reactors)

moreover imply a high phosgene holdup, which is undesirable for safety reasons. Low temperatures are also problematic because of the massive precipitation of the carbamoyl chloride formed as an intermediate, which decomposes rapidly at elevated temperatures. This involves the risk of blockage and caked deposits. Furthermore, cooling of the reactants and subsequent heating of the reaction mixture is disadvantageous in energy terms. To achieve economic space-time yields, it is necessary to work at elevated temperature in all stages of industrial processes for the preparation of organic isocyanates by the phosgenation of primary organic amines. However, at high temperatures, the solubility of phosgene in the reaction mixture decreases and with it the phosgene excess available for the reaction, since the reaction normally takes place in the liquid phase, but a large phosgene excess is required in order to obtain high yields of isocyanate. EP-A-0 716 079 describes the influence of pressure and temperature on the reaction and the phosgene excess. The lowering of phosgene excess at higher temperatures is generally countered by an increased reaction pressure.

DE-OS 17 68 439 describes a process for the continuous preparation of organic isocyanates which is characterized by the combination of a high temperature above 180° C. and a high pressure of 20 to 150 atm, together with a high phosgene concentration in the region of the reaction. The amount of phosgene introduced is 2.5 to 5.5 times the stoichiometric amount. The extremely high pressure and very high temperature are capable of producing acceptable space-time yields. The residence time of the reactants in the reaction zone is 5 to 60 s. The preferred solvent is chlorobenzene. The disadvantage of the process is the reduced yield and quality caused by the increased formation of by-products, especially ureas, due to the high temperature.

EP-A-0 065 727 describes a process employing a nozzle and a tubular reactor. In this process, organic monoisocyanates and polyisocyanates are continuously prepared in a one-stage reaction by the continuous combination of solutions of primary monoamines or polyamines in inert organic solvents with excess amounts of phosgene dissolved in an inert solvent, at pressures of from 10 to 1000 bar, preferably from 25 to 150 bar, and temperatures of from 120 to 300° C., preferably from 150 to 250° C., in a mixing chamber and optionally a downstream reaction zone, with continuous work-up. The phosgene solution, used in excess, is continuously introduced into a mixing chamber and the amine component, used in substoichiometric proportions, is introduced by means of a smooth jet nozzle. The smooth jet nozzle, which is essential for the process, has an inside diameter of from 0.1-30 mm. A differential pressure of at least 0.5 bar, preferably of from 1-200 bar, most preferably from 3-50 bar is maintained in the amine solution introduced through the nozzle. The molar ratio of phosgene to amino groups is from 2:1 to 30:1, preferably from 3:1 to 18:1. The post-reaction zone can be a tubular reactor, a multi-tube fixed-bed reactor or, for example, a series of stirred-tank reactors. The mean residence time in the mixing vessel and the downstream reaction zone is between 5 seconds and 5 minutes. The reaction mixture leaving the post-reaction zone is expanded into an expansion vessel at normal pressure in one or more stages, the temperature dropping by 50-150° C. The gas and liquid phases are separated in the expansion vessel. The solvent used is preferably chlorobenzene or o-dichlorobenzene.

GB-A-827 376 describes a continuous process for the preparation of aromatic isocyanates by the reaction of an amine in the free form in a solvent, or as a salt readily decomposable to the amine, suspended in a solvent, and a solution of phosgene in an inert solvent, under a pressure above $3 \cdot 10^5$ Pa.

In this disclosed process, the reactants are introduced simultaneously, with mixing, into the bottom end of a vertical tubular reactor. The reaction products rapidly rise to the top end of the tubular reactor. The liquid phase is collected in a tank from which it is withdrawn for isolation of the isocyanate. This tank can be a phase separating apparatus which is operated under the same pressure, communicates with the liquid outlet via an overflow tube and has a butterfly valve in the liquid outlet. The liquid separated off in the tank is introduced into a column operated under atmospheric pressure or excess pressure and elevated temperature, residual phosgene and hydrogen chloride being separated off in gaseous form at the top. Excess phosgene is condensed (preferably with cooling water) out of the hydrogen chloride/phosgene mixture separated off in the tank, and the hydrogen chloride separated off in this way is expanded and exhausted. The reactants are introduced into the tubular reactor by means of one common pump or two separate pumps or mixed in a Venturi mixing nozzle, preferably with separate inlets for the two reactants, and transferred from there to the tubular reactor. The temperature in the tubular reactor is described as 80 to 200° C. and the pressure is above $3 \cdot 10^5$ Pa, at most the vapor pressure of the reaction mixture and preferably from 15 to $20 \cdot 10^5$ Pa.

U.S. Pat. No. 3,226,410 describes a continuous process for the preparation of aromatic isocyanates by mixing a stream of an aromatic amine into a stream of phosgene in a tubular reactor with Reynolds numbers of more than 2100 (preferably from 5000 to 2,000,000) and at temperatures of from 60 to 90° C. and preferably of from 80 to 85° C. The amount of phosgene is at least 1 mol, preferably from 6 to 12 mol, per mol of amine. After preheating, if appropriate, the reaction solution is then transferred to a second reactor, especially a tank or column, which is at a temperature of from 110 to 135° C. and preferably of from 110 to 120° C. The amine concentration is from 2 to 25 wt. % and preferably from 5 to 10 wt. % and the phosgene concentration is from 10 to 100 wt. % and preferably from 10 to 60 wt. %. The pressure at which the phosgene stream is transferred to the tubular reactor is from 50 to 170 psig; the pressure of the amine stream has to be greater in order to prevent back-mixing. The liquid phase, which contains isocyanate, solvent, relatively small amounts of by-products, hydrogen chloride and phosgene dissolved in the solvent, is withdrawn from the second reactor separately from the gas phase, which contains hydrogen chloride, solvent, phosgene and traces of isocyanate. The solvents used are chlorinated hydrocarbons which are inert and have a lower boiling point than the isocyanate. Chlorobenzene is particularly preferred.

Under a pressure of 45 psig or more, the second reactor is followed by a holding tank and a buffer vessel from which material is transferred under continuous regulation to a column for the removal of excess phosgene. Phosgene, hydrogen chloride and solvent are drawn off at the top and recycled into the phosgene tank. The bottom product, composed of isocyanate and solvent, is passed on for separation of the solvent by distillation, preferably in one stage. The solvent separated from the isocyanate is used to absorb the residual phosgene from the hydrogen chloride stream. The phosgene drawn off from the second reactor and the buffer tank is condensed in two stages and recycled into the phosgene tank. The incondensable phosgene/hydrogen chloride mixture is transferred to a phosgene absorber into which solvent obtained from the solvent separation is introduced.

The unabsorbed gas, principally hydrogen chloride, is then reacted with water in an absorber to produce aqueous hydrochloric acid.

The tubular reactor should be constructed as a plugflow reactor without kinks, pockets or other internal fittings, which can produce dead zones, in order to prevent solids from settling out. The high Reynolds numbers and the design of the reactor as straight tubes should enable the liquid constantly to rinse caked deposits off the walls.

DE-A-27 47 524 describes a continuous process for the preparation of aromatic isocyanates in which the reactor is heated sufficiently to prevent added phosgene from causing cooling and hence forming caked deposits of the carbamoyl chloride intermediate on the reactor wall. A plugflow reactor composed of two coaxial tubes into which the two reactants, amine and phosgene, in an inert organic solvent, are separately introduced in counter-current and mixed at the end of the inner tube is described. Back-mixing into the feed zone is said to be eliminated, minimizing the formation of by-products. A steam jacket is used to control temperature and prevent the mixing zone from becoming blocked with the carbamoyl chloride intermediate. The required temperatures are said to be from 90 to 140° C. and the indicated temperatures are generally from 90 to 200° C. However, the starting temperature is 60 to 90° C. The upper pressure limit is determined by practical considerations. 2 atm is given as a comfortable pressure. The amine concentration in the inert solvent is given as 2 to 20% and preferably 5 to 10%. Dichlorobenzene is preferred as the inert solvent.

A tubular reactor is also the preferred apparatus for the process described in WO-A-96/16028 for the preparation of isocyanates with isocyanate as solvent. WO-A-96/16028 describes a continuous one-stage process wherein the primary amine, optionally dissolved in an inert organic solvent, is reacted with phosgene, 10 to 60 wt. % of which is dissolved in the isocyanate, based on the isocyanate/phosgene solution, at temperatures of from 60 to 180° C. and pressures of from 1 to 30 bar, to give the corresponding isocyanate. The molar ratio of phosgene to amine used is from 4:1 to 1:1 and the isocyanate used as solvent is free of solids and has a hydrolyzable chlorine value below 2%.

DE-A-198 17 691 discloses a two-stage process for the preparation of mixtures of diphenylmethane diisocyanates (MDI) and polyphenylenepolymethylene poly-isocyanates (PMDI), having a reduced content of chlorinated by-products and a reduced iodine color index. In this disclosed process, the corresponding mixtures of diphenylmethanediamines (MDA) and polyphenylenepolymethylenediamines (PMDA) are reacted with phosgene in the presence of at least one organic solvent, at elevated temperature, the excess phosgene and solvent are separated when phosgenation is complete, and the reaction product is thermally treated. The molar ratios of phosgene to hydrogen chloride in the holding apparatus of the second stage of the phosgenation are simultaneously 10 to 30:1 in the liquid phase and 1 to 10:1 in the gas phase. In the second stage of the phosgenation, the carbamoyl chlorides and amine hydrochlorides formed in the first stage of the phosgenation, i.e. in a static mixer, pass through a holding apparatus in which the amine hydrochlorides are phosgenated to the corresponding carbamoyl chlorides, and the carbamoyl chlorides are cleaved into the corresponding isocyanates and hydrogen chloride. The temperature of the first stage is conventionally from 40 to 150° C., preferably from 60 to 130° C. and most preferably from 90 to 120° C. The static mixers used for the first stage are preferably nozzles. Apart from mechanical stirrers and series of stirred-tank reactors, the holding apparatus used for the second stage is most preferably a column, especially a reaction column having predominantly <10 theoretical plates. It is particularly advantageous to operate the column in counter-current. The bottom temperature of the column is preferably from 80 to 120° C. and most preferably from 90 to 110° C. The top pressure of the column is preferably from 1.0 to 4.7 atm and most preferably from 2.0 to 3.7 atm.

U.S. Pat. No. 3,544,611 also describes a process for the preparation of organic isocyanates under a high pressure of from 10 to 50 bar using a reaction column. The first reaction step in the preparation of isocyanate, namely reaction between the amine and phosgene to give the carbamoyl chloride intermediate, is carried out in a loop reactor (mixing circuit). The second reaction step, namely decomposition of the carbamoyl chloride to the isocyanate, takes place in a reaction column downstream of the mixing circuit, a hydrogen chloride/phosgene mixture being obtained at the top of the column. Phosgene is condensed out of this mixture in two stages. The phosgene obtained is recycled into the top of the column. Phosgene is withdrawn from a liquid outlet in the rectifying section of the column and recycled into the reaction (mixing circuit).

Separation of the residual phosgene from the reaction mixture withdrawn from the bottom of the reaction column takes place in another column, where phosgene is withdrawn from the top, condensed in two stages analogously to the first column, and recycled into the mixing circuit of the reaction. The reaction to give the isocyanate is completed in the reaction column. It is commented that, surprisingly, higher yields of isocyanate are obtained by carrying out the reaction at higher pressures of at least 10 atm.

A reaction column is also used in DE-A-37 36 988, which describes a continuous process for the preparation of organic monoisocyanates or polyisocyanates in a one-stage reaction by reacting the amine, dissolved in an organic solvent, with phosgene, dissolved in an organic solvent, in a reaction column at a temperature below 150° C. The reaction mixture is passed through the reaction column continuously from bottom to top. The reaction column has at least 10 chambers separated from one another by perforated trays. The concentration of the amine in the inert solvent is from 5 to 40 wt. % and preferably from 7 to 20 wt. %. Preferred solvents are chlorobenzene or dichlorobenzene or mixtures thereof. Phosgene is used as a 30 to 65 wt. % solution or, preferably, a 40 to 65 wt. % solution in the inert solvent. The equivalent ratio of amine to phosgene is from 1:1.5 to 1:7, preferably from 1:2 to 1:5. The temperature at the top of the column is preferably from 70 to 130° C., more preferably from 90 to 125° C. and at most 150° C. The mean residence time in the reaction column is at most 120 minutes and preferably at most 60 minutes. The pressure in the column is from 1.2 to 3 bar abs and preferably from, 1.5 to 2.5 bar abs.

As holding apparatus, DE-A-37 44 001 proposes a perforated-tray column through which material flows from bottom to top and which has >10 perforated trays and preferably from 20 to 50 perforated trays, a residence time of max. 120 minutes and preferably of max. 60 minutes, a liquid speed of from 0.05 to 0.4 m/s and preferably of from 0.1 to 0.4 m/s, and gas speeds of from 2 to 20 m/s and preferably of from 3.5 to 10 m/s. The horizontally integrated perforated trays form 10 to 50 chambers. The top temperature of the reaction column is below 150° C., preferably from 70 to 130° C. and most preferably from 90 to 125° C. The top pressure of the column is from 1.2 to 3 bar (abs) and preferably from 1.5 to 2.5 bar (abs). A nozzle is used for the first phosgenation stage.

The processes cited above proceed with markedly higher space-time yields than the conventional cold-hot phosgenations. A disadvantage of these processes, as with the cold-hot phosgenations, is that the amine hydrochloride phosgenation and the carbamoyl chloride decomposition are carried out in one and the same reactor, which leads to longer residence times and higher phosgene holdups and promotes the secondary reaction of already formed isocyanate with amine to give ureas.

In many processes, the reaction of phosgene with amine is carried out in a loop reactor or recycle reactor into which, in addition to the amine and phosgene feed streams, optionally in a solvent, at least part of the reaction mixture is recycled. This dilution by recycling of the reaction mixture formed serves on the one hand to improve the ease of handling of the reaction mixture, which is attributable to the solvent action of the isocyanate to be prepared (DE-A-1 192 641), and mainly to control the temperature or improve the dissipation of heat in order to obtain lower temperatures. The reaction between amine and phosgene is strongly exothermic. If the reaction course and apparatus design are unfavorable, higher temperatures cause an increased formation of by-products, which in the case of toluene diisocyanate (TDI), leads to a loss of yield and the production of tar. Ureas are the main by-products obtained.

DE-A-26 24 285 describes a mixing circuit process for the continuous preparation of organic isocyanates from organic amines and phosgene in the presence of organic solvents in which the phosgene is admixed with the circulated reaction solution. The resulting reaction mixture and the amines or amine solution are introduced into the mixing and reaction zone in such a way as to produce an energy dissipation density of 5 to 1000 kJ per $m^3$ of reaction mixture recycled plus amine solution introduced. The reaction takes place at temperatures of from 90 to 220° C. and preferably of from 120 to 180° C. and in a pressure range of from 1 to 10 bar and preferably of from 1 to 3 bar. The residence times are from 10 to 180 minutes. The molar ratio of amine to phosgene is calculated so that from 1 to 10 mol and preferably from 1.3 to 4 mol of phosgene are present per amino group in the reaction mixture. The yields are from 88 to 98 wt. %, based on the amine used.

The mixing circuit process described in DE-A-26 24 285 is further developed in the process disclosed in EP-A-0 150 435. EP-A-0 150 435 describes a process for the continuous preparation of organic isocyanates by the reaction of organic amines with phosgene in the presence of organic solvents in which hydrogen chloride is separated off and part of the reaction mixture is circulated, wherein the hydrogen chloride content of the reaction mixture recycled after the separation of hydrogen chloride for the addition of amines is equal to or less than 0.5 wt. % and preferably from 0.01 to 0.4 wt. %, based on the total weight of the reaction mixture, before the addition of amines, and the molar ratio of phosgene to amine groups in the organic amines is from 12 to 200:1. The reaction is carried out at temperatures of from 100 to 220° C. and preferably of from 120 to 180° C. and in a pressure range of from 5 to 100 bar and preferably of from 15 to 50 bar.

Likewise, DE-A-34 03 204 is a further development of DE-A-26 24 285. A process is described for the continuous preparation of organic isocyanates, preferably polyisocyanates, by the reaction of organic amines, preferably polyamines, with phosgene in the presence of organic solvents, under a pressure of, e.g., 5 to 100 bar, at elevated temperatures of, e.g., 100 to 220° C., wherein part of the reaction mixture is circulated, preferably according to the natural circulation principle, the hydrogen chloride content of the reaction mixture before the addition of amines is less than 0.5 wt. %, based on the total weight of the reaction mixture, and the molar ratio of phosgene to amino groups in the organic amines is from 12 to 200:1.

DE-A-32 12 510 also describes a process for the continuous preparation of organic isocyanates using a recycle reactor. The primary organic amine, in a practically dispersed state, is brought into contact with an excess of phosgene at a manometric or excess pressure of 10 kg/cm$^2$, i.e. 10 bar, and a temperature of from 60 to 100° C., whereby a corresponding organic carbamoyl chloride is formed from the organic amine and intermediate hydrochloride, and hydrogen chloride is formed as a by-product. The conversion in this first stage is such that 30 to 70% of the carbamoyl chloride is converted to isocyanate. The reaction mixture is kept at a manometric or excess pressure of 10 kg/cm$^2$ and a temperature of 120 to 160° C., whereby conversion of the hydrochloride to the carbamoyl chloride is achieved and conversion of the carbamoyl chloride to the isocyanate is completed. The reaction takes place in a recycle reactor (recirculation line) or in a tank-like reaction vessel. In the first case, the phosgene together with the solvent is circulated in a tubular recirculation line and the amine is mixed in (mixing circuit). The residence time is from 30 to 120 minutes in the first stage and from 10 to 120 minutes in the second stage. The chosen solvent is o-dichlorobenzene.

GB-A-763 535 and DE-A-18 11 609 likewise describe loop reactors or recycle reactors (mixing circuits as reaction system). The organic isocyanate is prepared by the reaction of an amine with phosgene in a one-stage continuous reaction with the recirculation of isocyanate, solvent and unreacted phosgene. The sufficient pressure in the process described in GB-A-763 535 is 5 to 20 pounds per square inch, the reaction temperature is 90 to 180° C., the TDA concentration in the solvent is 5 to 30%, the stoichiometric phosgene excess is at least 25% and preferably 70 to 110%, and the solvents used are chlorinated aromatic hydrocarbons and preferably o-dichlorobenzene. In DE 18 11 609, the organic amine, optionally, in o-dichlorobenzene or another solvent, and excess phosgene are mixed under high shear stress into the circulating reaction mixture, it advantageously being possible, because of the mixing, to select conditions that differ from GB 763 535. The reaction pressure is preferably at least 1.8 to 14·10$^5$ Pa and preferably 4.2·10$^5$ Pa or 3.5·10$^5$ Pa. The preferred reaction temperature is given as 102 to 130° C. and for toluenediamine, as 90 to 120° C. The phosgene excess is from 50 to 200% and preferably 70%.

Recirculation is also utilized in GB-A-1 034 285, which describes a continuous process for the preparation of organic isocyanates by the reaction of phosgene with a primary polyamine in the presence of an inert organic solvent, the reactants being fed separately into a tubular reactor, where they are brought into contact, and a mixture of the same solvent, the reaction mixture and phosgene being recycled through this tubular reactor. The reactor used can be a circuit of two cylindrical tanks between which the reaction mixture is circulated, or an annular tubular reactor. The reaction mixture can be stirred by means of stirrers. The temperature in the tubular reactor is 8 to 50° C. The pressure is atmospheric pressure or slightly above. The concentration of the metered primary polyamine in the solvent is 2 to 20 wt. %. The amount of phosgene added to the forced circulation stream is 5 to 20 mol of phosgene per mol of amino groups in the polyamine solution added. The inert organic solvent used is chlorobenzene or o-dichlorobenzene.

JP-A-57 048 954 describes a process for the preparation of organic isocyanates wherein the solution of the primary amine is introduced just upstream of a static mixer or propeller mixer located in a recycle reactor. A solution of phosgene in organic isocyanate circulates in the recycle reactor.

DE-A-100 27 779 claims a process for the preparation of isocyanates by the reaction of amine with phosgene wherein the isocyanate is used as solvent and the reaction is carried out in a reaction column, all or part of the condensed phase at the bottom of the reaction column being recycled into the rectifying section of the reaction column. The number of theoretical separating plates in the reaction column is 5 to 60. The temperature is −20° C. to 300° C. and the absolute pressure is 0.2 to 60 bar.

A disadvantage of the loop reactor or mixing circuit processes in energy terms is the low temperatures in the first stage and the high temperatures in the second stage. As the reaction between an organic amine and phosgene is strongly exothermic, intense cooling is necessary in the first step in order to maintain the desired reaction temperature. The second reaction, namely decomposition of the carbamoyl chloride to the isocyanate, is markedly endothermic, so the reaction mixture has to be heated again in the second stage.

A particular disadvantage, however, especially in a one-stage procedure, is the markedly lower chemical yields compared with straight-through processes, because already formed isocyanate reacts with amine to give ureas in the mixing circuit due to back-mixing. To suppress this secondary reaction, a low maximum steady-state isocyanate concentration is often imposed, which in turn means low space-time yields.

EP-A-0 570 799 describes a process wherein the reaction between amine and phosgene to give the isocyanate is carried out in the gas phase. Gas phase phosgenation is known for the preparation of aliphatic diisocyanates (EP-A-0 289 840), aromatic diisocyanates (EP-A-0 570 799), cyclic diisocyanates (EP-A-1 078 918) and triisocyanates (EP-A-0 749 958). EP-A-0 749 958, EP-A-0 676 392 and EP-A-0 289 840 describe processes for the preparation of aliphatic diisocyanates and triisocyanates by gas phase phosgenation wherein the mixing of the reactants at the inlet to the described tubular reactor is effected by means of nozzles or a combination of nozzle and annular gap between nozzle and tube. The essential criterion for mixing here is given as a Reynolds number RE of >4700 in the tube. A jet mixer is indicated in EP-A-0 570 799 for the preparation of aromatic diisocyanates by gas phase phosgenation.

Disadvantages of gas phase phosgenation are that the reaction components have to be evaporated, the reactions take place at very high temperatures, so gas phase phosgenation is restricted to the conversion of amines that can be evaporated without decomposition, and the reaction mixture and the isocyanate formed are subjected to thermal stress, resulting in increased by-product formation and reduced yields.

There have also been many attempts to minimize the fundamental disadvantages of the liquid phase phosgenation processes outlined above by preparing the appropriate carbamoyl chlorides in a first stage under optimized conditions for this reaction, and then decomposing them in a second stage or further stages to give the isocyanates to be prepared.

DE-A-2 252 068 describes a process for the preparation of organic isocyanates from amine and phosgene wherein the amine, preheated to a temperature below its decomposition point at superatmospheric pressure, is reacted with preheated phosgene in the presence of an excess of an organic isocyanate as solvent, at temperatures and pressures such that the reaction proceeds in a homogeneous liquid phase, and then, in a second stage, the intermediate organic carbamoyl chloride is thermally cleaved at a lower pressure. In one preferred embodiment, the first stage is carried out adiabatically. The reaction components are fed in at temperatures ranging from 120 to 180° C. The temperature of the reaction mixture at the outlet is kept at 180 to 250° C. and the pressure at 100 to 300 atm. The residence time of the components in the first reaction zone should be 5 to 150 seconds. The second reaction stage is carried out isothermally. The inlet temperature is 120 to 250° C. and the pressure 3 to 30 atm. The residence time is 3 to 30 minutes. The isocyanate withdrawn from the second stage is cooled to 50 to 80° C. before recycling.

WO-A-2004/056756 describes a two-stage or multistage process which produces isocyanates with very high chemical yields and high space-time yields and with a low phosgene holdup, this being attributable, according to the Claim, to the fact that, as well as the intended formation of carbamoyl chloride, the process according to the invention takes particular account of the formation of amine hydrochloride that takes place as a secondary reaction in the reaction of the amine with the phosgene.

WO-A-2004/056756 cites I. I. Konstantinov, A. I. Kormucheshkina, Zhurnal Prikladnoi Khimii, 49 (3), pp. 596-599, 1976, who teaches that the phosgenation of amine hydrochloride is very slow and represents the rate-determining step of the whole reaction cycle leading to the isocyanate. Konstantinov also presents kinetic measurements and quantifies the reaction rates, according to which the rate of the hydrochloride phosgenation reaction is considerably slower than that of the free amine.

WO-A-2004/056756 also refers to GB-A-1 212 249, according to which the formation of amine hydrochloride also leads to a loss of yield of isocyanate due to urea formation, and maintains that, because the solubility of amine hydrochlorides is very low in the corresponding reaction mixtures and also in the majority of commercially available solvents, the problem of solid production is moreover drastically exacerbated by hydrochloride formation.

WO-A-2004/056756 likewise refers to DE-A-33 23 882, which describes a continuous process for the hot phosgenation of amine hydrochloride, or a mixture thereof with carbamoyl chloride, suspended in solvent, with excess phosgene at a temperature of between 80° C. and 200° C. and preferably of between 100° C. and 180° C. The process is characterized in that the solids are retained in the reactor by means of a suitable separating device and the isocyanate formed during the reaction, in solution in the solvent, is withdrawn continuously from the reactor. The solids are preferably separated off with a filter. As correctly maintained in WO-A-2004/056756, the disadvantages of the hydrochloride phosgenation process described in DE 33 23 882 are the laborious handling of solids, the risk of blockage of piping and especially control valves and flow meters, the long residence time, which demands large apparatuses with a high phosgene holdup, and the drastic reaction conditions and lower yields.

WO-A-2004/056756 additionally refers to DE-A-24 04 773, which describes a process for the preparation of mono-, di- and/or polyisocyanates from organic primary amines and phosgene wherein the primary amines are mixed with at least 3 mol of phosgene per amino group in the absence of a solvent, the reaction mixture simultaneously being comminuted to a mean particle size of 1-100 μm, and the resulting suspension of carbamoyl chloride and amine hydrochloride in phosgene is converted to the corresponding isocyanates at temperatures of 100 to 180° C. and preferably of 120 to 160° C. and pressures of 14 to 55 bar and preferably of 21 to 41 bar. This is a two-stage process wherein, in the first stage, the primary amine and phosgene starting materials are mixed at temperatures of −30 to 60° C. and preferably of 0 to 50° C., at normal pressure or, preferably, at elevated pressure and especially at 14 to 55 bar, the particles simultaneously being comminuted to a mean size of 1 to 100 μm and preferably of 1 to 50 μm. The amine is introduced into the phosgene as a liquid, a melt or optionally a powder. Various mixing and comminuting devices are described. The second stage comprises reacting amine hydrochloride with phosgene to give carbamoyl chloride and decomposing the latter into isocyanate and hydrogen chloride in a pressure vessel at temperatures of 100-180° C. and preferably of 120 to 160° C. and pressures of 14-55 bar and preferably of 21 to 41 bar. As correctly maintained in WO-A-2004/056756, this process is very expensive and uneconomic on the industrial scale.

The basis of the process described in WO-A-2004/056756 is that, contrary to the general teaching, the second reaction, i.e. the phosgenation of the amine hydrochloride, proceeds at high phosgene concentrations and elevated temperatures with a high reaction rate. High pressures are thus favorable for this reaction because they imply high phosgene concentrations in the liquid phase. Furthermore, elevated temperatures are favorable for achieving high space-time yields.

The process described in WO-A-2004/056756 for the preparation of polyisocyanates by the reaction of organic amines with phosgene is characterized in that the reaction is carried out in at least three stages, the first stage being carried out in a mixer, the second stage in at least one holding apparatus and the third stage in at least one material separating apparatus, and the pressure in each subsequent stage being lower than in the previous stage.

In the first stage of the process described in WO-A-2004/056756, basically the amine is converted to carbamoyl chloride and amine hydrochloride. In the second stage, basically the amine hydrochloride formed in the first stage is converted to carbamoyl chloride. In the third stage, basically the carbamoyl chloride is separated into isocyanate and hydrogen chloride. In the process described, the reaction between organic amine and phosgene is carried out in three or more stages in an inert solvent, preferably toluene or chlorobenzene, dichlorobenzene or mixtures thereof, and with excess phosgene, the pressure being reduced at each stage. The first phosgenation stage involves a static mixer and preferably a nozzle. The pressure upstream of the nozzle is preferably from 3 to 70 bar and more preferably from 15 to 45 bar. The pressure difference across the nozzle is at least 0.5 bar. The temperature in the first stage is preferably 80 to 190° C. and more preferably from 90 to 150° C. The second stage involves one or more holding apparatuses and preferably one holding apparatus that is operated at a pressure of 2.5 to 35 bar and preferably of 15 to 35 bar and temperatures of from 80 to 190° C. and preferably of from 90 to 150° C., and wherein the pressure downstream of the nozzle being expanded to the pressure of the holding apparatus of the second stage via a valve or other device suitable for the purpose. The reactor of the third stage of the process described is operated at a pressure of 2 to 20 bar and preferably of 3.5 to 16 bar and temperatures of 80 to 190° C., the pressure downstream of the holding reactor of the second stage being expanded to the pressure of the third reactor via a valve or other device suitable for the purpose.

The advantage of the process according to WO-A-2004/056756 lies in the fact that, in contrast to the conventional processes according to the otherwise described state of the art, the two reaction steps, phosgenation of the amine hydrochloride to carbamoyl chloride and decomposition of the carbamoyl chloride to isocyanate and hydrogen chloride, are partially or completely carried out in separate stages or reactors, and also that the formation of amine hydrochloride that takes place as a secondary reaction in the reaction of the amine with the phosgene is taken particularly into account, in the adjustment of the reaction conditions. Thus, by the mutually independent adjustment of the optimal pressure and optimal temperature for each particular reaction and by the choice of the most favorable reactor design in each case it is possible to achieve for very high chemical yields, very high space-time yields and at the same time a very low phosgene holdup.

WO-A-2004/056756 refers several times to the fact that in each case the pressure of the subsequent stage shall be chosen to be lower than that of the previous stage. The process according to WO-A-2004/056756 thus necessarily has at least three different pressure stages.

SUMMARY OF THE INVENTION

The object of the present invention is to develop a multi-stage process which produces isocyanates with very high chemical yields and high space-time yields and with a low phosgene holdup. It has been found that the mixing of the educts, amine and phosgene, is very important for the yield of the process and the avoidance of unwanted solid formation. It is therefore essential to provide a process for the preparation of isocyanates wherein the mixing can be optimized independently of the throughput, because some industrial processes have considerable variations in throughput.

It has been found, surprisingly, that the partial reactions can also be carried out extensively separately, as described in WO-A-2004/056756, if the pressure of the second stage is equal to or greater than that of the first stage. It has additionally been found that, by using a dynamic mixer, conditions that differ from WO-A-2004/056756 can advantageously be selected to the effect that the mechanically driven mixing devices can be loaded within very wide limits without a loss of efficacy in terms of the intended purpose, namely that of always creating optimal mixing conditions for the reactants of the first stage. Thus, by using a dynamic mixer, it is always possible to ensure optimal mixing conditions, even when the throughput varies or is deliberately changed. This is impossible when using nozzles or static mixers.

DETAILED DESCRIPTION OF THE INVENTION

The invention relates to a process for the preparation of isocyanates by the reaction of organic amine with phosgene in which the reaction is carried out in at least three stages. The first stage is carried out in a dynamic mixer. The second stage is carried out in at least one reactor. The third stage is carried out in at least one material separating apparatus. The pressure in the reactor of the second stage is greater than or equal to the pressure in the dynamic mixer. The pressure in the at least one material separating apparatus is less than the pressure in the reactor of the second stage.

In the first stage of the process according to the invention, basically the amine is converted to carbamoyl chloride and amine hydrochloride. In the second stage, basically the amine hydrochloride formed in the first stage is converted to carbamoyl chloride. In the third stage, basically the carbamoyl chloride is separated into isocyanate and hydrogen chloride. In the process according to the invention, the reaction between organic amine and phosgene is carried out in three or more stages in an inert solvent, preferably toluene or chlorobenzene, dichlorobenzene or a mixture thereof, and with excess phosgene. An essential feature of the invention is that the mixing takes place in a dynamic mixer, the pressure in the second stage reactor being greater than or equal to the pressure in the dynamic mixer, and the pressure in the separating apparatus being less than the pressure in the reactor of the second stage.

The first phosgenation stage takes place in a dynamic mixer, preferably in a mixer reactor such as that described, e.g., in EP 0 291 819 B1 in column 1/line 44 to column 2/line 49 and whose detailed construction is described in connection with FIGS. 1 and 2 at column 4/line 34 to column 5/line 46, preferably in a mixer reactor such as that described in EP 0 830 894 B1 in paragraphs 0005 to 0011/0012 to 0014 and whose detailed construction is described in connection with FIGS. 1 to 4 in paragraphs 0016 to 0022.

Suitable mixer reactors are those which:
(1) have a mixing chamber and an upstream partition chamber in their housings of essentially rotational symmetry;
(2) permit introduction of at least the first material in the axis of the mixing chamber, e.g. via a bent tube entering the side of the partition chamber wall;
(3) permit the at least second material stream to pass into the partition chamber and reach the mixing chamber via a large number of parallel perforations concentric to the axis of the mixer reactors;
(4) have a mixing chamber containing rotor elements driven via a shaft and stator elements connected to the housing;
(5) have a mixing chamber outlet which can form an impeller that conveys the reaction mixture into the outlet tube of the stirred-tank reactor; and
(6) make it possible to mix the components under optimal conditions, independently of the throughput, by means of the external mechanical drive.

The mixer reactors disclosed in EP 0 830 894 B1 advantageously differ from the mixer reactors disclosed in EP 0 291 819 B1 in that:
a) bolts are allocated to each of their perforations arranged with rotational symmetry relative to the axis of the mixing chamber;
b) these bolts can be moved by means of a common carrier ring and a shaft inserted through the housing of the partition chamber;
c) if caked deposits and/or blockages form in the perforations, the latter can be cleared by axial displacement of the bolts, and
d) non-productive times for cleaning the perforations can thus be reduced to a few seconds.

However, basically any dynamic mixer that assures intimate mixing by means of mechanically driven parts, for example, rotary mixing devices and especially multistage centrifugal pumps, are suitable for use in the first stage of the process of the present invention.

The pressure in the dynamic mixer of the first stage is preferably from 3 to 70 bar and particularly preferably from 3 to 35 bar. The temperature in the first stage is preferably from 80 to 220° C. and particularly preferably from 90 to 180° C.

The second stage is carried out in at least one reactor, i.e. a holding apparatus suitable for carrying out chemical reactions, which is hydraulically connected to the dynamic mixer of the first stage. If there are two or more reactors in operation, these can be connected to one another in parallel or in series. The pressure in the second stage is preferably from 3 to 70 bar and particularly preferably from 3 to 37 bar. The temperature in the second stage is preferably from 80 to 220° C. and particularly preferably from 90 to 180° C.

Suitable types of reactor for the second stage are tubular reactors, stirred-tank reactors and non-mixed holding apparatuses. The reactor can also be provided with a pumped circuit, which in turn can contain a heat exchanger for adjusting the reactor temperature. Tubular reactors are particularly preferred.

In the material separating apparatus of the third stage, the carbamoyl chloride is converted to the isocyanate and the reaction mixture is separated into a gas phase and a liquid phase. The gas phase is essentially composed of hydrogen chloride and, depending on the pressure and temperature, optionally, part of the excess phosgene used and part of the solvent vapors. The material separating apparatus of the third stage of the process according to the invention is operated at a pressure of from 0.5 to 20 bar and preferably of from 0.5 to 16 bar. Downstream of the reactor of the second stage, the pressure is expanded to the pressure of the material separating apparatus of the third stage via a valve or other device suitable for the purpose. The temperature of the third stage is from 80 to 220° C. In addition to heat exchangers with separate gas discharge, stirred-tank reactors, series of stirred-tank reactors, perforated-tray columns or other apparatuses for separating materials, a particularly suitable type of reactor for the material separating apparatus of the third stage is a (reaction) tower, for example, a (reaction) tower such as that disclosed in DE-37 36 988 C1 at column 3, lines 2-64. The material separating apparatus of the third stage can also be utilized for removing the excess phosgene from the reaction mixture. Like the reactor of the second stage, the material separating apparatus of the third stage can also be disadvantageously large. In this case it can alternatively take the form of two or more identical or different apparatuses, preferably, a combination of heat exchanger with separate gas discharge and (reaction) tower, or a combination of (reaction) tower/towers and (reaction) column, which are preferably connected in series in both cases.

The reaction mixture discharged from the third stage is then preferably worked up by conventional methods to remove any phosgene still present and to separate off the solvent. This can be followed by other work-up steps; for example, in the case of the preparation of TDI, the crude TDI is subjected to separation of the high boilers and to purification by distillation. Phosgene, hydrogen chloride and optionally solvent are separated in known manner from the vapors from the material separating apparatus of the third stage and, if appropriate, the reactor of the second stage, and optionally recycled.

The solvents used are preferably chlorinated aromatic hydrocarbons, such as chlorobenzene, dichlorobenzene, trichlorobenzene or mixtures thereof; aromatic or aliphatic hydrocarbons, such as toluene, xylene, benzene, pentane, hexane, heptane, octane, cyclohexane or biphenyl; ketones, such as 2-butanone or methyl isobutyl ketone; esters, such as diethyl isophthalate, ethyl acetate or butyl acetate; or nitrites, such as acetonitrile; and sulfolane.

The advantages of the process according to the invention is that, in contrast to the conventional processes according to the state of the art include:

1. the two reaction steps, phosgenation of the amine hydrochloride to carbamoyl chloride and decomposition of the carbamoyl chloride to isocyanate and hydrogen chloride, are partially or completely carried out in separate stages or reactors, making it possible for very high chemical yields, very high space-time yields and at the same time a very low phosgene holdup to be achieved by the mutually independent adjustment of the optimal pressure and optimal temperature for each particular reaction and by the choice of the most favorable reactor design in each case; and 2. the good mixing of the reactants in the first reaction stage, which is necessary for the rapid reaction between amine and phosgene to give carbamoyl chloride and hydrogen chloride with the production of very small amine hydrochloride particles, is always assured in this stage, extensively independently of load, by the use of a dynamic mixer, because the mechanically driven mixing devices can be loaded within very wide limits without loss of the ability to create optimal mixing conditions for the reactants of the first stage.

The process of the present invention can be carried out adiabatically or isothermally. The differences in apparatus design are determined on the basis of the conditions of all the reactions, particularly those of the phosgenation of the amine hydrochloride to carbamoyl chloride and the decomposition of the carbamoyl chloride to isocyanate and hydrogen chloride. While high pressures are required for the phosgenation of the amine hydrochloride, low pressures are advantageous for the decomposition of the carbamoyl chloride. Shorter residence times can be chosen for the amine hydrochloride phosgenation reactor than for the carbamoyl chloride decomposition, markedly reducing the overall phosgene holdup. Removal of the hydrogen chloride formed is advantageous for the decomposition of the carbamoyl chloride because the carbamoyl chloride/isocyanate equilibrium is thereby shifted in favor of the desired isocyanate. Special attention can be paid to this by choosing a heat exchanger with separate gas discharge or a combination of (reaction) tower/towers and (reaction) column, connected in series, as apparatuses for the third stage. Excess phosgene can also be removed at the same time. However, removal of the excess phosgene in this stage is not compulsory and it can also be carried out in a subsequent stage.

In contrast, the removal of hydrogen chloride from the reactor of the second stage would be very disadvantageous because (1) the by-product formation of the isocyanate with amine hydrochloride is favored by shifting the carbamoyl chloride/isocyanate equilibrium towards the isocyanate; (2) the phosgene required for phosgenation of the amine hydrochloride would also be removed together with the hydrogen chloride; and (3) hydrogen chloride gas released from the reaction mixture, and particularly evaporating phosgene, cause cooling of the reaction mixture, which could lead to the massive precipitation of solid carbamoyl chloride and amine hydrochloride.

For good chemical yields afforded by low by-product formation, the reaction conditions of the first and second stages required for the rapid reactions between amine and phosgene to give carbamoyl chloride and hydrogen chloride and between hydrogen chloride and amine to give amine hydrochloride, as well as the reaction of the amine hydrochloride with phosgene to give carbamoyl chloride, are high pressures, which make it possible to achieve high phosgene concentrations in the liquid phase and hence large phosgene excesses. Also, good mixing of the reactants in the first stage is always necessary for the production of very small amine hydrochloride particles, which is why the process according to the invention uses a dynamic mixer to allow the introduction of large mixing energies extensively independently of load.

As shown for the first time in WO-A-2004/056756, dissolved amine hydrochloride and very small amine hydrochloride particles react very rapidly with phosgene at high phosgene concentrations and elevated temperatures, in contradiction of the general teaching of the prior art. Surprisingly, however, contrary to WO-A-2004/056756, correspondingly reactive amine hydrochloride particles can be produced and reacted when the pressure in the reactor of the second stage is greater than or equal to the pressure in the dynamic mixer, and the pressure in the at least one material separating apparatus of the third stage is smaller than the pressure in the reactor of the second stage. Dissolved amine and the amine hydrochloride particles obtained therefrom react very rapidly with phosgene in the reactor of the second stage and therefore do not need a long residence time. High phosgene concentrations are advantageous here. Higher pressures do not have a disadvantageous effect on the phosgenation of the amine hydrochloride, so higher phosgene concentrations in the liquid phase can preferably be obtained by means of higher pressures. Heatable reactors for the second stage are advantageous because they enable compensation for any drops in temperature due to the endothermic decomposition of the carbamoyl chloride.

The main reaction in the third stage, i.e. the decomposition of the carbamoyl chloride to isocyanate and hydrogen chloride, is a pressure-dependent equilibrium reaction. It is shifted by low pressures in favor of the desired isocyanate. As this reaction does not require phosgene, the low phosgene concentrations in the liquid phase that are characteristic of low pressures do not interfere. To the contrary, they result in a low phosgene holdup in the material separating apparatus of the third stage, which is favorable in terms of safety. The phosgene holdup in the overall process, but optionally also in individual apparatuses, can thus be markedly reduced in comparison with conventional processes in a series of stirred-tank reactors or a reaction tower.

The phosgenation of the amine hydrochloride does not have to go to completion in the second stage. By the same token, the decomposition of the carbamoyl chloride can start in the second stage. Preferably, however, the design of the reactor of the second stage with respect to residence time and other process engineering parameters is such that the phosgenation of the amine hydrochloride is as complete as possible and the decomposition of the carbamoyl chloride has advanced as little as possible.

If the phosgenation of the amine hydrochloride and the decomposition of the carbamoyl chloride are carried out in one stage or in one reactor, according to the state of the art, the pressure required for the phosgenation of the amine hydrochloride causes a low conversion of the carbamoyl chloride to isocyanate and hence long residence times. A high phosgene concentration and long residence times (large reaction volumes) in turn mean a very large phosgene holdup. This also occurs at high pressures and temperatures, which give rise to safety concerns. Spatial separation of the two reactions—the phosgenation of the amine hydrochloride at high pressure in the second phosgenation stage and the decomposition of the carbamoyl chloride at low pressure in the third phosgenation stage—affords high chemical yields, high space-time yields and especially a low phosgene holdup in the overall process and optionally also in the individual apparatuses.

Spatial separation of the first and second stages is not absolutely necessary because a high pressure increases the phosgene concentration in the liquid phase, which benefits both the first reaction between amine and phosgene and the second reaction between amine hydrochloride and phosgene. In addition, the mixing of the reactants takes place very rapidly in a dynamic mixer, so, even if the first and second stages of the process take place in a common apparatus, firstly the mixing of the reactants takes place in the region of the dynamic mixer, and then the subsequent reaction takes place in the holding region of the common apparatus.

Furthermore, the process can be carried out in all stages at elevated temperature and optionally also isothermally. In particular, compared with conventional cold-hot phosgenations, this achieves high space-time yields and hence low phosgene holdups and uses smaller apparatuses coupled with higher chemical yields. Also, an appreciable amount of energy is saved by avoiding the need to cool the reaction mixture in the first stage and then reheat it in the second and subsequent stages. By avoiding the precipitation of amine hydrochloride as a solid, it is possible to avoid long residence times, as can be achieved in some cases only by a recirculation system (loop reactors). Although the recirculation system also has a low phosgene holdup, for example as a series of stirred-tank reactors, it is characterized by an increased formation of by-products, especially ureas. To avoid urea formation, the amine or isocyanate concentration has to be kept low, resulting in very low space-time yields.

The temperatures and pressures used depend to some extent on the amine used. Preferably, the phosgene excess should be at least 70% of the stoichiometric input in the case of diphenylmethane diisocyanates (MDI) and/or polyphenylene-polymethylene polyisocyanate (PMDI) or mixtures of the two, at least 150% of the stoichiometric input in the case of toluene diisocyanate (TDI) and isophorone diisocyanate (IPDI), and at least 250% of the stoichiometric input in the case of hexamethylene diisocyanate (HDI).

The residence time in the first stage (dynamic mixer) is conventionally very short and defined by the apparatus design. It ranges from 0.1 to 60 seconds and preferably from 0.1 to 10 seconds. The mean residence time in the reactor of the second stage can preferably be between 1 second and 30 minutes. Mean residence times of 5 seconds to 10 minutes are particularly preferred and mean residence times of between 10 seconds and 5 minutes are very particularly preferred. The mean residence time of the reaction mixture in the material separating apparatus or in the corresponding combined apparatus of the third stage, for example the heat exchanger with separate gas discharge, the (reaction) tower or the combination of (reaction) tower and (reaction) column, connected in series, also depends on their design and loading. It is preferably at most 60 minutes for the liquid phase.

The amine concentration in the inert solvent also depends on the amine and solvent used. It can be from 5 to 60 wt. % and preferably from 25 to 50 wt. % in the case of diphenylmethanediamine (MDA) and/or polyphenylenepolymethylenepolyamines (PMDA) or mixtures of the two, from 5 to 30 wt. % and preferably from 15 to 30 wt. % in the case of toluenediamine (TDA), from 5 to 50 wt. % and preferably from 15 to 30 wt. % in the case of hexamethylenediamine (HDA), and from 5 to 30 wt. % and preferably from 10 to 20 wt. % in the case of isophoronediamine (IPDA), based in each case on the weight of the solution. The phosgene concentration in the inert solvent can be from 5 to 70 wt. % and preferably from 30 to 70 wt. %, based on the weight of the solution. It is preferable to use the same solvent as for the amine. It is also possible to omit a solvent altogether.

The invention will be described in greater detail by means of the Examples which follow.

EXAMPLES

Example 1

In a mixer reactor corresponding to that described in EP-A-0 830 894, 10 t/h of an 18.0 wt. % solution of toluenediamine (TDA) in ortho-dichlorobenzene at a temperature of 80° C. and 17 t/h of a 61.9 wt. % solution of phosgene in ortho-dichlorobenzene at a temperature of −10° C. were mixed and reacted continuously under a power input of 35 kW. The pressure in the reactor was 7.6 bar and the temperature in the reactor outlet was 96.3° C.

After a mean residence time of 2.1 sec in the reactor, the reaction mixture was conveyed via the reactor impeller into a downstream tubular reactor with a heating jacket and operating at 7.7 bar, where it was kept at >95° C. for a residence time of 14 sec, after which it was expanded via a control valve into a heatable reaction tower divided by perforated trays into chambers and operating at a top pressure of 1.7 bar, which was the phase separating apparatus.

The reaction mixture was fed into the bottom of the reaction tower and, as it travelled through the apparatus, was heated uniformly by means of segment heaters so that the separately exhausted gas phase, and the liquid phase, left the apparatus at a temperature of 125° C.

The gas phase drawn off contained a mixture (11.2 t/h) of phosgene (7.2 t/h; 64.3 wt. %), hydrogen chloride (2 t/h; 17.8 wt. %), ortho-dichlorobenzene (2 t/h; 17.8 wt. %) and small amounts of different low boilers (carbon tetrachloride, chloroform, nitrogen, carbon monoxide, carbon dioxide). This mixture was passed on for a hydrogen chloride/phosgene separation in known manner.

The liquid phase overflowing from the tower (15.8 t/h) contained toluene diisocyanate (2.48 t/h; 15.7 wt. %), ortho-dichlorobenzene (12.6 t/h; 81 wt. %), phosgene (0.4 t/h; 2.6 wt. %), hydrogen chloride (<20 kg/h; <0.1 wt. %) and small amounts of high boilers (<100 kg/h; <0.6 wt. %).

A TDI yield of 96.7% was obtained, based on the TDA used.

Example 2

In a mixer reactor corresponding to that described in EP-A-0 830 894, 76.5 kg/h of a 30.0 wt. % solution of MDA (average molecular weight: 242 g/mol) in monochlorobenzene at a temperature of 106° C. and 88.3 kg/h of a 45 wt. % solution of phosgene in monochlorobenzene at a temperature of 4° C. were mixed and reacted continuously under a power input of 0.75 kW. The pressure in the reactor was 18.5 bar and the temperature in the reactor outlet was 128° C.

After a mean residence time of 3 sec in the reactor, the reaction mixture was conveyed via the reactor impeller into a downstream, well-insulated tubular reactor operating at 19 bar, where it was kept in the region of the reactor outlet temperature for a residence time of 99 sec, after which, at a temperature of 123° C., it was expanded via a control valve into a heatable heat exchange tube operating at a top pressure of 0.5 bar, which was the phase separating apparatus for the carbamoyl chloride cleavage.

The reaction mixture was fed into the bottom of the heat exchange tube, where it cooled to 97° C. due to the expansion and the endothermic carbamoyl chloride cleavage, and then, as it travelled through the tube, it was heated so that the separately exhausted gas phase, and the liquid phase, left the apparatus at a temperature of 130° C.

The gas phase drawn off contained a mixture (100.5 kg/h) of phosgene (17.5 kg/h; 17.4 wt. %), hydrogen chloride (15.7 kg/h; 15.6 wt. %), monochlorobenzene (67.3 kg/h; 67.0 wt. %) and small amounts of various low boilers (carbon tetrachloride, chloroform, nitrogen, carbon monoxide, carbon dioxide), and was passed on for a hydrogen chloride/phosgene separation in known manner.

The liquid phase overflowing from the heat exchange tube (64.4 kg/h) with a mean residence time of 162 sec contained MDI (28.7 kg/h; 44.6 wt. %), monochlorobenzene (34.9 kg/h; 54.2 wt. %), phosgene (0.4 kg/h; 0.6 wt. %) and small amounts of dissolved hydrogen chloride (0.4 kg/h; 0.6 wt. %).

The liquid phase withdrawn from the heat exchange tube was freed of hydrogen chloride, phosgene and monochlorobenzene according to the state of the art and subjected to thermal after treatment. The mixture of diphenylmethane diisocyanates and polyphenylenepolymethylene diisocyanates prepared in this way was characterized by the following product properties:

| | |
|---|---|
| Viscosity at 25° C. | 193 mPas |
| NCO content | 31.0% |
| Color E 430 | 0.093[1)] |
| Color E 520 | 0.016[1)] |

[1)]1.0 g of the isocyanate obtained was dissolved in chlorobenzene and diluted to 50 ml with chlorobenzene. The extinction of the resulting solution was determined at wavelengths of 430 nm and 520 nm with a Dr. Lange LICO 300 photometer.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of isocyanate by the reaction of an organic amine with phosgene in at least three stages comprising:
   a) a first stage conducted in a dynamic mixer,
   b) a second stage conducted in at least one reactor, and
   c) a third stage conducted in at least one material separating apparatus
   in which (1) the second stage reactor pressure is greater than the first stage dynamic mixer pressure, and (2) the third stage material separating apparatus pressure is lower than the pressure in the reactor of the second stage.

2. The process of claim 1 in which the isocyanate produced is diphenylmethane diisocyanate (MDI), polyphenylenepolymethylene polyisocyanate (PMDI), mixtures of MDI and PMDI, toluene diisocyanate (TDI), hexamethylene diisocyanate (HDI) or isophorone diisocyanate (IPDI).

3. The process of claim 1 in which a tubular reactor, a stirred-tank reactor or a holding apparatus without movable internal fittings is used as the second stage reactor.

4. The process of claim 1 in which the residence time in the second stage reactor is from 1 second to 30 minutes.

5. The process of claim 1 in which a heat exchanger with separate gas discharge, or a reaction column, or a reaction tower, or a combination of at least one reaction tower and at least one reaction column connected in series, is used as the third stage material separating apparatus.

6. The process of claim 1 in which phosgene is separated off in the third stage material separating apparatus.

7. The process of claim 1 in which the second stage reactor pressure is increased by means of a pump or other device capable of building-up pressure.

8. The process of claim 1 in which the pressure in the first stage dynamic mixer is from 3 to 70 bar, the second stage reactor pressure is from greater than 3 to 70 bar, and the third stage material separating apparatus pressure is from 0.5 to 20 bar.

9. The process of claim 1 in which the temperature in the first stage dynamic mixer, the second stage reactor, and the third stage material separating apparatus is from 80 to 220° C.

10. The process of claim 1 in which an aromatic hydrocarbon or a chlorinated aromatic hydrocarbon is used as a solvent.

* * * * *